United States Patent
Gebert et al.

(10) Patent No.: US 9,259,380 B2
(45) Date of Patent: Feb. 16, 2016

(54) MEANS FOR DYEING AND/OR MATTING KERATINIC FIBRES CONTAINING NOVEL 1,4 DIAMINOANTHRAQUINONE DYES

(71) Applicant: Henkel AG & Co. KGaA, Duesseldorf (DE)

(72) Inventors: Antje Gebert, Duesseldorf (DE); Astrid Kroos, Monheim (DE); Ralph Nemitz, Juechen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/484,218

(22) Filed: Sep. 11, 2014

(65) Prior Publication Data

US 2015/0007851 A1    Jan. 8, 2015

(30) Foreign Application Priority Data

Mar. 14, 2012  (DE) .......................... 10 2012 203 981

(51) Int. Cl.
*A61Q 5/10*   (2006.01)
*A61K 8/35*   (2006.01)
*C09B 1/26*   (2006.01)
*A61Q 5/06*   (2006.01)

(52) U.S. Cl.
CPC ............... *A61K 8/355* (2013.01); *A61Q 5/065* (2013.01); *A61Q 5/10* (2013.01); *C09B 1/262* (2013.01)

(58) Field of Classification Search
CPC ......... A61Q 5/065; A61Q 5/10; A61K 8/355; C09B 1/51; C09B 1/262
USPC .......................................................... 8/405
See application file for complete search history.

(56) References Cited

U.S. PATENT DOCUMENTS

| | | |
|---|---|---|
| 3,576,587 A | 4/1971 | Kalopissis et al. |
| 3,597,254 A | 8/1971 | Graser et al. |
| 3,617,163 A | 11/1971 | Kalopissis et al. |
| 4,226,784 A | 10/1980 | Kalopissis et al. |
| 2007/0166256 A1* | 7/2007 | Shiroyama et al. ......... 424/70.2 |

FOREIGN PATENT DOCUMENTS

| | | |
|---|---|---|
| EP | 2263642 A2 | 12/2010 |
| FR | 1326406 * | 5/1963 |
| GB | 1053300 | 12/1966 |
| WO | 2011/160864 A2 | 12/2011 |

OTHER PUBLICATIONS

STIC Search Report dated Mar. 4, 2015.*
English translation (Feb. 5, 2015) of the Patent FR 1326406.*
PCT International Search Report (PCT/EP2013/054178) dated Jul. 5, 2013.

* cited by examiner

*Primary Examiner* — Eisa Elhilo
(74) *Attorney, Agent, or Firm* — David K. Benson

(57) ABSTRACT

Agents for coloring and/or matting keratinic fibers, in particular human hair, include in a cosmetic carrier at least one specific substituted 1,4-diaminoanthraquinone derivative of formula (I), wherein the residues (R2, R4) mutually independently denote a grouping of formula (II). The cosmetic method of using these agents can be for producing intense blue shades and for matting keratin fibers.

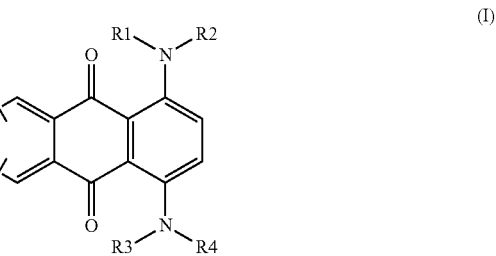

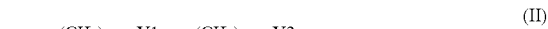

9 Claims, No Drawings

MEANS FOR DYEING AND/OR MATTING KERATINIC FIBRES CONTAINING NOVEL 1,4 DIAMINOANTHRAQUINONE DYES

FIELD OF THE INVENTION

The present invention generally relates to agents for coloring and/or matting keratin-containing fibers, in particular human hair, which include novel derivatives of 1,4-diaminoanthraquinone. The invention furthermore relates to the use of these agents and to a corresponding method.

BACKGROUND OF THE INVENTION

In general, it is either substantive dyes or oxidation dyes which are used for coloring keratinic fibers. Although intense and sustained colorings may be achieved with oxidation dyes, the color generally develops under the influence of oxidizing agents such as for example $H_2O_2$, which may in some cases result in damage to the fibers. Moreover, some oxidation dye precursors or certain mixtures of oxidation dye precursors may have a sensitizing effect in people with sensitive skin. Substantive dyes are applied under milder conditions. The disadvantage thereof, however, is that the colorings frequently are not sustained as long as those produced from oxidation dyes, in particular when the hair is washed, but also in relation to external influences, such as sunlight or reactive environmental chemicals, such as for example swimming pool water.

One particular challenge for hair coloring using substantive dyes is uniformly coloring frequently pretreated hair, such as for example bleached or permed hair, in which the fibers have highly variable levels of prior damage at different lengths or in differently treated areas. During the actual coloring, the coloring agent may exhibit uneven coloring behavior on hair suffering differing levels of prior damage, but repeated hair washing can also wash out the dyes to varying extents in the different areas of hair, leading to a non-uniform and thus unwanted coloring result.

It is therefore desirable to provide coloring agents for keratinic fibers, in particular human hair, which exhibit good applicational properties with regard to color depth and fastness characteristics, such as in particular light, abrasion and washing fastness as well as sweat and cold perming fastness. Finally, it is particularly desirable to provide coloring agents with a good equalizing capacity.

If keratinic fibers are to be oxidatively lightened or blonded, substantive dyes may also be used in combination with oxidizing agents. Hair is generally blonded by applying aqueous hydrogen peroxide solutions, either alone or in combination with further oxidizing agents acting as bleach activators such as for example persulfate salts, onto the keratin fibers. In order to achieve a sufficient blonding action, such agents are conventionally strongly alkalized, the pH generally being between 9 and 10.5. Under the action of the oxidizing agents, the melanins, the natural, color-imparting pigments of hair fibers, are oxidatively destroyed and the fibers are consequently decolorized or lightened. Melanins are located in the cortex of the hair fibers and may be divided into two classes of pigments. Eumelanins are the first, brownish-black class of pigments, while the reddish pigments with a higher sulfur content are known as pheomelanins. Due to the different levels of resistance of the various types of pigment to oxidizing agents, the pheomelanins and eumelanins are, however, not always uniformly decolorized. In addition, in darker hair with an elevated melanin content, the melanins may only be partially or incompletely broken down and therefore a residual proportion of the color-imparting pigments remains in the hair after blonding. In these cases, the residual content of melanins still present in the hair after the oxidative process results in a yellowish to reddish shift in shade. Therefore, in particular when blonding darker hair, a color shift towards warm tints occurs.

Users do not normally desire such color shifts towards warm tints. This color shift is therefore usually counteracted by tinting in the corresponding complementary color according to color theory. The aim here is to achieve a silvery cool appearance of the bleaching result. A person skilled in the art refers to this as matting. Blue substantive dyes may in particular be used for matting blond shades with an orange cast. In order to ensure the completest possible attenuation of the orange color appearance, it is advantageous for the blue dye itself to have no red content in its coloring. Dyes in pure blue and in particular in grayish blue shades are thus better suited to matting an orange blonding result than are blue dyes with a violet cast. However, despite the numerous blue dyes usable in hair coloring products, no dyes are known from the prior art which optimally meet all the above-stated requirements. There is accordingly still a major need for novel substantive dyes with corresponding coloring and matting properties.

GB 1 053 300 describes a process for coloring hair in which 1,4-diaminoanthraquinone derivatives may be used which bear one or two dialkylaminoalkyl substituents on the amino groups thereof. These dyes are intended to have a good coloring capacity, elevated water solubility and elevated lightfastness. The range of shades extends from intense blue via blue-violet to mauve, pink and blue-green. Blue colorings with a gray cast cannot, however, be obtained by means of these dyes. DE 1 644 306 discloses a method for producing 1,4-diaminoanthraquinone derivatives which bear an aminoalkylamino substituent on each of the two nitrogen atoms of the anthraquinone ring. The dyes produced in the context of this method are intended to have an elevated affinity for keratin fibers and good washing fastness. The range of shades achieved with the dyes extends from yellow to blue. Blue color shades with a gray shift cannot be achieved with these derivatives either.

It is particularly desirable to find novel matting dyes which meet the conventional fastness requirements placed on substantive dyes, have good storage stability and furthermore have a blue color shade tending strongly towards grayish without any red content. It is intended to be possible to use the dyes not only in the form of a post-treatment after the oxidative blonding process but, in single-stage methods, also simultaneously with the oxidizing agent, for which reason they must additionally have good stability towards the oxidizing agents.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

The applicant has now surprisingly found that the specifically substituted 1,4-diaminoanthraquinone derivatives of general formula (I) optimally meet the above-described requirements for novel matting dyes.

An agent for coloring and/or matting keratinic fibers, in particular human hair, includes in a cosmetic carrier at least one 1,4-diaminoanthraquinone derivative of formula (I),

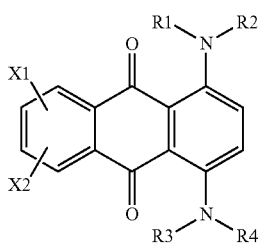

(I)

in which R1, R3 mutually independently denote a hydrogen atom, a $C_1$-$C_6$ alkyl group, a $C_2$-$C_6$ alkenyl group, a hydroxy-$C_2$-$C_6$-alkyl group, a polyhydroxy-$C_2$-$C_6$-alkyl group, a cyano-$C_1$-$C_6$-alkyl group, a halo-$C_1$-$C_6$-alkyl group, an aryl-$C_1$-$C_6$-alkyl group, a heteroaryl-($C_1$-$C_6$)-alkyl group, an aryl group, a heteroaryl group, an amino-($C_2$-$C_6$)-alkyl group, a $C_1$-$C_6$-alkylamino-$C_2$-$C_6$-alkyl group or a $C_1$-$C_6$-dialkylamino-$C_2$-$C_6$-alkyl group, R2, R4 mutually independently denote a grouping of formula (II), $$-(CH_2)_n-Y1-(CH_2)_m-Y2 \qquad (II)$$

in which Y1 denotes an oxygen atom (—O—), a sulfur atom (—S—), an amide group —CONR5- or a group —NR5-, Y2 denotes a hydrogen atom, a $C_2$-$C_6$ alkenyl group, a hydroxyl group, a $C_1$-$C_6$ alkoxy group, a hydroxy-$C_2$-$C_6$-alkoxy group or a group —NR5R6, n denotes an integer from 2 to 6, m denotes an integer from 1 to 6, R5, R6 mutually independently denote a hydrogen atom, a $C_1$-$C_6$ alkyl group, a $C_2$-$C_6$ alkenyl group, or a hydroxy-$C_2$-$C_6$-alkyl group, and X1, X2 mutually independently denote a hydrogen atom, a hydroxyl group, a $C_1$-$C_6$ alkoxy group, a $C_1$-$C_6$ alkyl group, a $C_2$-$C_6$ alkenyl group, a hydroxy-$C_2$-$C_6$-alkyl group, a polyhydroxy-$C_2$-$C_6$-alkyl group, a cyano-$C_1$-$C_6$-alkyl group, an amino group, a $C_1$-$C_6$-alkylamino group, a di-$C_1$-$C_6$-alkylamino group, an amino-($C_2$-$C_6$)-alkyl group, a $C_1$-$C_6$-alkylamino-$C_2$-$C_6$-alkyl group, a di-$C_1$-$C_6$-alkylamino-$C_2$-$C_6$-alkyl group, a $C_1$-$C_6$-alkoxy-$C_2$-$C_6$-alkyl group, a $C_1$-$C_6$-alkoxy-$C_2$-$C_6$-alkyloxy group, a nitro group, a carboxy group, a sulfonic acid group or a halogen atom.

A method for matting keratinic fibers in which, directly before use, a cosmetic agent (A1) for oxidative lightening including 0.5 to 20 wt. % hydrogen peroxide is mixed with an agent (A2), this ready-to-use agent is applied onto the keratin fibers, left on the keratin fibers for a period of 5 to 60 minutes, preferably of 15 to 45 minutes, and then rinsed back out, and then a post-treatment agent (B) is applied onto the keratin fibers, left on the keratin fibers for a period of 2 to 45 minutes, preferably of 5 to 30 minutes, and then rinsed back out, wherein the agent (A2) and/or the agent (B) is the agent.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present invention firstly provides an agent for coloring and/or matting keratinic fibers, in particular human hair, including in a cosmetic carrier at least one 1,4-diaminoanthraquinone derivative of formula (I),

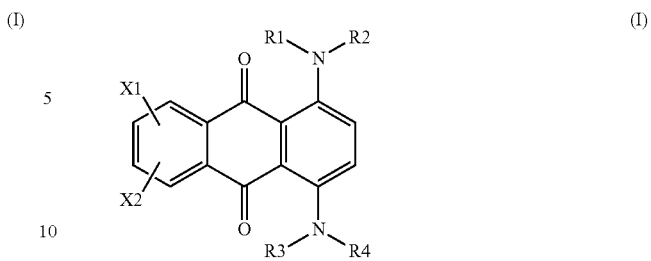

(I)

in which
R1, R3 mutually independently denote a hydrogen atom, a $C_1$-$C_6$ alkyl group, a $C_2$-$C_6$ alkenyl group, a hydroxy-$C_2$-$C_6$-alkyl group, a polyhydroxy-$C_2$-$C_6$-alkyl group, a cyano-$C_1$-$C_6$-alkyl group, a halo-$C_1$-$C_6$-alkyl group, an aryl-$C_1$-$C_6$-alkyl group, a heteroaryl-($C_1$-$C_6$)-alkyl group, an aryl group, a heteroaryl group, an amino-($C_2$-$C_6$)-alkyl group, a $C_1$-$C_6$-alkylamino-$C_2$-$C_6$-alkyl group or a $C_1$-$C_6$-dialkylamino-$C_2$-$C_6$-alkyl group,
R2, R4 mutually independently denote a grouping of formula (II), $$-(CH_2)_n-Y1-(CH_2)_m-Y2 \qquad (II)$$

in which
Y1 denotes an oxygen atom (—O—), a sulfur atom (—S—), an amide group —CONR5- or a group —NR5-,
Y2 denotes a hydrogen atom, a $C_2$-$C_6$ alkenyl group, a hydroxyl group, a $C_1$-$C_6$ alkoxy group, a hydroxy-$C_2$-$C_6$-alkoxy group or a group —NR5R6,
n denotes an integer from 2 to 6,
m denotes an integer from 1 to 6,
R5, R6 mutually independently denote a hydrogen atom, a $C_1$-$C_6$ alkyl group, a $C_2$-$C_6$ alkenyl group, or a hydroxy-$C_2$-$C_6$-alkyl group, and
X1, X2 mutually independently denote a hydrogen atom, a hydroxyl group, a $C_1$-$C_6$ alkoxy group, a $C_1$-$C_6$ alkyl group, a $C_2$-$C_6$ alkenyl group, a hydroxy-$C_2$-$C_6$-alkyl group, a polyhydroxy-$C_2$-$C_6$-alkyl group, a cyano-$C_1$-$C_6$-alkyl group, an amino group, a $C_1$-$C_6$-alkylamino group, a di-$C_1$-$C_6$-alkylamino group, an amino-($C_2$-$C_6$)-alkyl group, a $C_1$-$C_6$-alkylamino-$C_2$-$C_6$-alkyl group, a di-$C_1$-$C_6$-alkylamino-$C_2$-$C_6$-alkyl group, a $C_1$-$C_6$-alkoxy-$C_2$-$C_6$-alkyl group, a $C_1$-$C_6$-alkoxy-$C_2$-$C_6$-alkyloxy group, a nitro group, a carboxy group, a sulfonic acid group or a halogen atom.

Keratinic fibers, keratin-containing fibers or keratin fibers should here be taken to mean furs, wool, feathers and in particular human hair. Although the agents according to the invention are primarily suitable for lightening keratin fibers, there is no reason in principle why they should not also be used in other fields.

The phrase "coloring keratin fibers" used according to the invention includes any kind of color modification of the fibers. In particular, color modifications falling within the terms tinting, blonding, oxidative coloring, semipermanent coloring, permanent coloring and temporary coloring are included. Color modifications which provide a lighter coloring result than the initial color, such as for example blonding with coloring, are explicitly also included according to the invention. The phrase "matting keratin fibers" is taken to mean counteracting undesired shifts in shade which occur during oxidative color modification of keratin fibers, in particular during blonding or bleaching processes. The aim of matting is to attenuate the orange to reddish color appearance caused by incomplete blonding and to produce a silvery cool perceived color after the blonding process. The active substances used during matting may be applied in the form of a post-treatment step after blonding or bleaching of the keratin fibers.

It is, however, likewise possible to apply the active substances used for matting to the keratin fibers in the course of a single-stage method together with the blonding agent or the bleaching agent. Active substances suitable for matting which may be used are substantive dyes, either alone or in the dye mixture, having suitable color properties. It is furthermore likewise possible to use substantive dyes in combination with oxidation dye precursors (developers and couplers) for matting.

The agents according to the invention include the compounds of formula (I) in a cosmetic carrier. This cosmetic carrier is preferably aqueous, alcoholic or aqueous-alcoholic. Carriers suitable for the purpose of hair treatment are for example creams, emulsions, gels or also surfactant-containing foaming solutions, such as for example shampoos, foam aerosols or other preparations which are suitable for use on the hair. It is, however, also possible for storage purposes to provide a formulation which assumes pulverulent or also tablet form. Said formulation is then mixed prior to use in an aqueous solvent or with organic solvents or with mixtures of water and organic solvents to obtain the mixture for use. An aqueous carrier includes for the purposes of the invention at least 40 wt. %, in particular at least 50 wt. %, water. For the purposes of the present invention, aqueous-alcoholic solutions should be taken to be aqueous solutions including 3 to 70 wt. % of a $C_1$-$C_4$ alcohol, in particular ethanol or isopropanol. The agents according to the invention may additionally include further organic solvents, such as for example 4-methoxybutanol, ethyl diglycol, 1,2-propylene glycol, n-propanol, n-butanol, n-butylene glycol, glycerol, diethylene glycol monoethyl ether and diethylene glycol mono-n-butyl ether. Any water-soluble organic solvents are preferred for this purpose. Preferred agents according to the invention are characterized in that they additionally include a nonaqueous solvent, wherein preferred agents according to the invention include the solvent in a concentration of 0.1 to 30 wt. %, preferably in a concentration of 1 to 20 wt. %, particularly preferably in a concentration of 2 to 10 wt. %, in each case relative to the agent.

Substituents R1 to R6, X1 and X2 of the compound of formula (I) are exemplified below: examples of a $C_1$-$C_6$ alkyl group are the groups methyl, ethyl, propyl, isopropyl, n-butyl, s-butyl and t-butyl, n-pentyl and n-hexyl. Propyl, ethyl and methyl are preferred alkyl residues. Examples of a $C_2$-$C_6$ alkenyl group are vinyl, allyl, but-2-enyl, but-3-enyl and isobutenyl, preferred $C_2$-$C_6$ alkenyl residues are vinyl and allyl. Preferred examples of a hydroxy-$C_1$-$C_6$-alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is more preferred. Examples of a polyhydroxy-$C_2$-$C_6$-alkyl group are the 2,3-dihydroxypropyl group, 3,4-dihydroxybutyl group and the 2,4-dihydroxybutyl group. Preferred examples of cyano-$C_1$-$C_6$-alkyl groups are the cyanomethyl group, the 2-cyanoethyl group and the 3-cyanopropyl group. Halo-$C_1$-$C_6$-alkyl groups which are preferred according to the invention are the chloromethyl group, the bromomethyl group, the fluoromethyl group, the 2-chloroethyl group, the 2-bromoethyl group, the 2-fluoromethyl group, the 2-chloropropyl group, the 2-bromopropyl group, the 2-fluoropropyl group, the 3-chloropropyl group, the 3-bromopropyl group and the 3-fluoropropyl group. Preferred examples of aryl-$C_1$-$C_6$-alkyl groups are benzyl, 1-phenethyl and 2-phenylethyl. Examples of heteroaryl-$C_1$-$C_6$-alkyl groups which may be mentioned are the imidazol-1-ylmethyl group, the imidazol-2-ylmethyl group, the imidazol-4-ylmethyl group, the pyridin-2-yl group, the pyridin-3-yl group and the pyridin-4-ylmethyl group. Aryl groups which are preferred according to the invention are the phenyl group and the naphthyl group. Examples of a heteroaryl group are the pyridin-2-yl group, the pyridin-3-yl group, the pyridin-4-yl group, the imadzol-1-yl group, the imidazol-2-yl group and the imidazol-4-yl group. Examples of an amino-($C_2$-$C_6$)-alkyl group which may be mentioned are the 2-aminoethyl group, the 2-aminopropyl group, the 3-aminopropyl group, the 2-aminobutyl group, the 3-aminobutyl group and the 4-aminobutyl group. Examples of a $C_1$-$C_6$-alkylamino-$C_2$-$C_6$-alkyl group are the 2-(methylamino)ethyl group, the 2-(ethylamino)ethyl group, the 2-(propylamino)ethyl group, the 3-(methylamino)propyl group, the 3-(ethylamino)propyl group, the 3-(propylamino)propyl group, the 4-(methylamino)butyl group, the 4-(ethylamino)butyl group and the 4-(propylamino)butyl group. Examples of a $C_1$-$C_6$-dialkylamino-$C_2$-$C_6$-alkyl group are the 2-(dimethylamino)ethyl group, the 2-(diethylamino)ethyl group, the 2-(dipropylamino)ethyl group, the 3-(dimethylamino)propyl group, the 3-(diethylamino)propyl group, the 3-(dipropylamino)propyl group, the 4-(dimethylamino)butyl group, the 4-(diethylamino)butyl group and the 4-(dipropylamino)butyl group. $C_1$-$C_6$ alkoxy groups which are preferred according to the invention are the methoxy group or the ethoxy group. Examples according to the invention of a hydroxy-$C_2$-$C_6$-alkoxy group are the 2-hydroxyethoxy group, the 2-hydroxypropoxy group (or the 2-hydroxypropyloxy group), the 3-hydroxypropoxy group (or the 3-hydroxypropyloxy group), the 2-hydroxybutoxy group (or the 2-hydroxybutyloxy group), the 3-hydroxybutoxy group (or the 3-hydroxybutyloxy group) and the 4-hydroxybutoxy group (or the 4-hydroxybutyloxy group). Examples of a $C_1$-$C_6$ alkylamino group which may be mentioned are methylamino, ethylamino, n-propylamino, n-butylamino and isopropylamino. Examples of the di-$C_1$-$C_6$-alkylamino group are dimethylamino, diethylamino, dipropylamino and dibutylamino, wherein dimethylamino and diethylamino are preferred. Preferred examples of $C_1$-$C_6$-alkoxy-$C_2$-$C_6$-alkyl groups according to the invention are the 2-(methoxy)ethyl group, the 2-(ethoxy)ethyl group, the 2-(propoxy)ethyl group, the 3-(methoxy)propyl group, the 3-(ethoxy)propyl group, the 3-(propoxy)propyl group, the 4-(methoxy)butyl group, the 4-(ethoxy)butyl group and the 4-(propoxy)butyl group. Examples according to the invention of a preferred $C_1$-$C_6$-alkoxy-$C_2$-$C_6$-alkyloxy group are the 2-methoxyethoxy group, the 2-methoxypropoxy group, the 3-methoxypropoxy group, the 2-methoxybutoxy group, the 3-methoxybutoxy group, the 4-methoxybutoxy group, 2-ethoxyethoxy group, the 2-ethoxypropoxy group, the 3-ethoxypropoxy group, the 2-ethoxybutoxy group, the 3-ethoxybutoxy group, the 4-ethoxybutoxy group, 2-propoxyethoxy group, the 2-propoxypropoxy group, the 3-propoxypropoxy group, the 2-propoxybutoxy group, the 3-propoxybutoxy group and the 4-propoxybutoxy group. Examples of halogen atoms are F, Cl, Br or I atoms, wherein Br and Cl atoms are particularly preferred. Compounds of the general formula (I), in which the substituents X1 and X2 mutually independently represent a hydrogen atom, a hydroxyl group, a $C_1$-$C_6$ alkoxy group, a $C_1$-$C_6$ alkyl group, an amino group or a halogen atom are particularly suitable for matting and are therefore preferred.

The shift in shade involving an orange cast of blonded keratin fibers may above all be effectively counteracted if the compounds of formula (I) used for this purpose are those in which the substituents X1 and X2 mutually independently denote a hydrogen atom or a $C_1$-$C_6$ alkoxy group.

A preferred embodiment of the present invention is accordingly an agent for coloring and/or matting keratinic fibers which is characterized in that it includes at least one compound of formula (I), in which X1 and X2 mutually independently denote a hydrogen atom, a hydroxyl group, a $C_1$-$C_6$ alkoxy group, a $C_1$-$C_6$ alkyl group, an amino group, or a halogen atom, preferably mutually independently denote a hydrogen atom or a $C_1$-$C_6$ alkoxy group.

It is particularly preferred for X1 and X2 both to denote a hydrogen atom, or alternatively for X1 to denote a hydrogen atom and X2 a methoxy group.

Compounds of formula (I), in which the residues R1 and R3 mutually independently denote a hydrogen atom, a $C_1$-$C_6$ alkyl group, a $C_2$-$C_6$ alkenyl group, or a hydroxy-$C_2$-$C_6$-alkyl group have likewise proved particularly suitable with regard to the applicational properties thereof. R1 and R3 more preferably mutually independently denote a hydrogen atom or a $C_1$-$C_6$ alkyl group. R1 and R3 particularly preferably both denote a hydrogen atom.

In formula (II), Y1 preferably denotes an oxygen atom (—O—), amide group —CONR5- or a group —NR5-. Y1 more preferably denotes an oxygen atom (—O—) or a group —NR5-. Dyes which are very highly suitable according to the invention with elevated affinity for keratin fibers are above all also those compounds of formula (I), in which R2 and R4 in each case denote a grouping of formula (II), in which Y2 denotes a hydrogen atom, a hydroxyl group, a $C_1$-$C_6$ alkoxy group, or a group —NR5R6.

The residues R5 and R6 preferably mutually independently denote a hydrogen atom or a $C_1$-$C_6$ alkyl group, particularly preferably mutually independently denote a hydrogen atom or a methyl group.

Compounds, of formula (I) which have proved particularly suitable for solving the problem of the invention are also those in which Y2 denotes a hydrogen atom, a hydroxyl group, a methoxy group or an amino group (with R5 and R6 being hydrogen).

A further preferred embodiment is an agent for coloring and/or matting keratinic fibers which is characterized in that it includes at least one compound of formula (I), in which R1 and R3 in each case denote a hydrogen atom and R2 and R4 mutually independently in each case denote a grouping of formula (II),

—(CH$_2$)$_n$—Y1-(CH$_2$)$_m$—Y2   (II)

in which

Y1 denotes an oxygen atom (—O—), an amide group —CONR5- or a group —NR5-,

Y2 denotes a hydrogen atom, a hydroxyl group, a $C_1$-$C_6$ alkoxy group or a group —NR5R6, n denotes an integer from 2 to 6, m denotes an integer from 1 to 6, R5, R6 mutually independently denote a hydrogen atom or a $C_1$-$C_6$ alkyl group.

In the course of the work leading to the present invention, it has surprisingly been found that the nature of formula (II) has a very decisive influence on substantivity and, in this connection, also on the fastness characteristics of the dyes. The residues R2 and R4 of general formula (I) mutually independently necessarily in each case denote a grouping of formula (II)

—(CH$_2$)$_n$—Y1-(CH$_2$)$_m$—Y2   (II)

wherein the formula (II) in each case includes two alkylene groups, the length of which is defined by the numbers n and m. The affinity of the dyes of formula (I) for keratin fibers can be still further increased by optimizing chain lengths. It has been found that intense colorings with good matting performance may in particular be obtained if n denotes the number 3. An advantageous effect on the intensity of the colorings is likewise obtained if m denotes the numbers 2 or 3.

A further particularly preferred embodiment is therefore an agent for coloring and/or matting keratinic fibers which is characterized in that it includes at least one compound of formula (I), in which R2 and R4 mutually independently denote a grouping of formula (II), in which n in each case denotes the number 3.

Symmetrical compounds of formula (I) are most readily synthetically obtainable. Symmetrical compounds of formula (I), in which the residues R1 and R3 and the residues R2 and R4 represent identical substituents are thus preferred. More preferred compounds of formula (I) in this connection are those in which the residues R1 and R3 in each case denote a hydrogen atom and the residues R2 and R4 represent identical substituents.

A particularly preferred embodiment is furthermore an agent for coloring and/or matting keratinic fibers which is characterized in that it includes at least one compound of formula (I), in which R1 and R3 in each case denote a hydrogen atom, R2 and R4 denote identical residues and R2 and R4 in each case denote a grouping of formula (II),

—(CH$_2$)$_n$-Y1-(CH$_2$)$_m$-Y2   (II)

in which

Y1 denotes an oxygen atom (—O—) or a group —NR5-,

Y2 denotes a hydrogen atom, a hydroxyl group, a $C_1$-$C_6$ alkoxy group or a group —NR5R6, n denotes the number 3, m denotes the numbers 2 or 3, and R5, R6 mutually independently denote a hydrogen atom or a $C_1$-$C_6$ alkyl group.

A further preferred embodiment are agents for coloring and/or matting keratinic fibers which are characterized in that they include at least one compound of the general formula (I) which is selected from 1,4-bis[(2-methoxyethyl)amino]-9,10-dihydroanthracene-9,10-dione

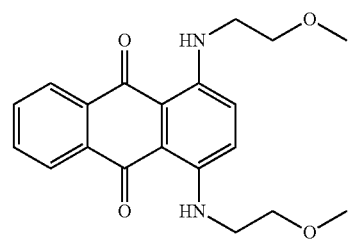

1,4-bis[(2-ethoxyethyl)amino]-9,10-dihydroanthracene-9,10-dione 1,4-bis[(2-propoxyethyl)amino]-9,10-dihydroanthracene-9,10-dione 1,4-bis[(3-methoxypropyl)amino]-9,10-dihydroanthracene-9,10-dione

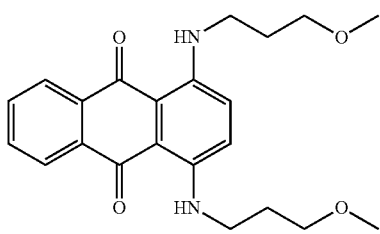 [SMILES: COCCCNc1ccc(NCCCOC)c2c1C(=O)c1ccccc1C2=O]

1,4-bis[(3-ethoxypropyl)amino]-9,10-dihydroanthracene-9,10-dione
1,4-bis[(3-propoxypropyl)amino]-9,10-dihydroanthracene-9,10-dione
6-methoxy-1,4-bis[(2-methoxyethyl)amino]-9,10-dihydroanthracene-9,10-dione

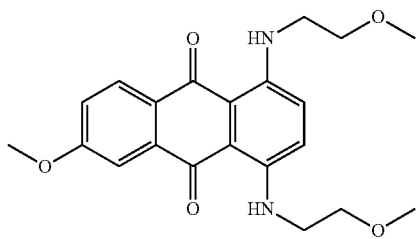

6-methoxy-1,4-bis[(2-ethoxyethyl)amino]-9,10-dihydroanthracene-9,10-dione
6-methoxy-1,4-bis[(2-propoxyethyl)amino]-9,10-dihydroanthracene-9,10-dione
6-methoxy-1,4-bis[(3-methoxypropyl)amino]-9,10-dihydroanthracene-9,10-dione

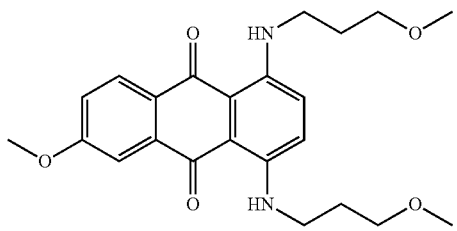

6-methoxy-1,4-bis[(3-ethoxypropyl)amino]-9,10-dihydroanthracene-9,10-dione
6-methoxy-1,4-bis[(3-propoxypropyl)amino]-9,10-dihydroanthracene-9,10-dione
1,4-bis({[2-(2-hydroxyethoxy)ethyl]amino})-9,10-dihydroanthracene-9,10-dione

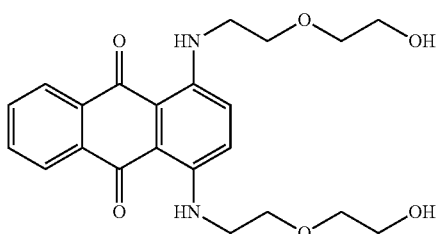

1,4-bis({[3-(2-hydroxyethoxy)propyl]amino})-9,10-dihydroanthracene-9,10-dione
1,4-bis({[2-(3-hydroxypropoxy)ethyl]amino})-9,10-dihydroanthracene-9,10-dione
1,4-bis({[3-(3-hydroxypropoxy)propyl]amino})-9,10-dihydroanthracene-9,10-dione
6-methoxy-1,4-bis({[2-(2-hydroxyethoxy)ethyl]amino})-9,10-dihydroanthracene-9,10-dione

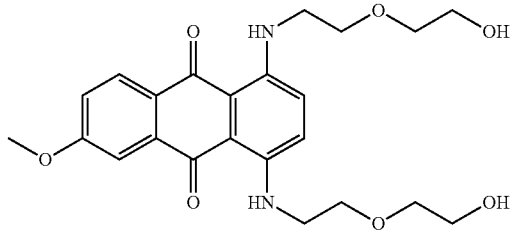 [SMILES: COc1ccc2c(c1)C(=O)c1c(NCCOCCO)ccc(NCCOCCO)c1C2=O]

6-methoxy-1,4-bis({[3-(2-hydroxyethoxy)propyl]amino})-9,10-dihydroanthracene-9,10-dione
6-methoxy-1,4-bis({[3-(3-hydroxypropoxy)ethyl]amino})-9,10-dihydroanthracene-9,10-dione
6-methoxy-1,4-bis({[3-(3-hydroxypropoxy)propyl]amino})-9,10-dihydroanthracene-9,10-dione
1,4-bis({2-[(2-hydroxyethyl)amino]ethyl}amino)-9,10-dihydroanthracene-9,10-dione
1,4-bis({2-[(3-hydroxypropyl)amino]ethyl}amino)-9,10-dihydroanthracene-9,10-dione

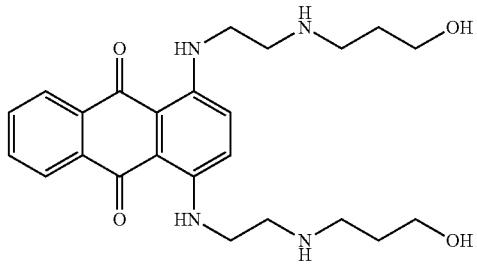 [SMILES: O=C1c2ccccc2C(=O)c2c(NCCNCCCO)ccc(NCCNCCCO)c21]

1,4-bis({3-[(2-hydroxyethyl)amino]propyl}amino)-9,10-dihydroanthracene-9,10-dione
1,4-bis({3-[(3-hydroxypropyl)amino]propyl}amino)-9,10-dihydroanthracene-9,10-dione
1,4-bis({2-[(2-aminoethyl)amino]ethyl}amino)-9,10-dihydroanthracene-9,10-dione

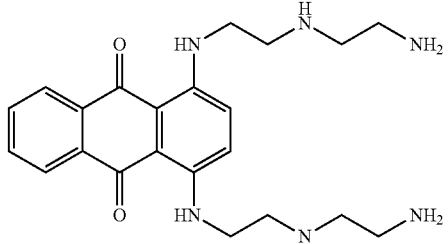

1,4-bis({2-[(3-aminopropyl)amino]ethyl}amino)-9,10-dihydroanthracene-9,10-dione
1,4-bis({3-[(2-aminoethyl)amino]propyl}amino)-9,10-dihydroanthracene-9,10-dione
1,4-bis({3-[(3-aminopropyl)amino]propyl}amino)-9,10-dihydroanthracene-9,10-dione N-methyl-3-[(4-{[2-(methylcarbamoyl)ethyl]amino}-9,10-dioxo-9,10-dihydroanthracen-1-yl)amino]propanamide

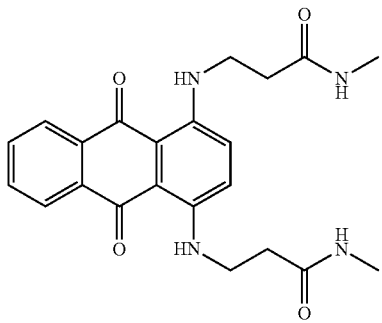 [SMILES: CNC(=O)CCNc1ccc(NCCC(=O)NC)c2c1C(=O)c1ccccc1C2=O]

N-methyl-4-[(4-{[3-(methylcarbamoyl)propyl]amino}-9,10-dioxo-9,10-dihydroanthracenyl)amino]butanamide
N-ethyl-3-[(4-{[2-(ethylcarbamoyl)ethyl]amino}-9,10-dioxo-9,10-dihydroanthracen-1-yl)amino]propanamide
N;N-dimethyl-3-[(4-{[2-(dimethylcarbamoyl)ethyl]amino}-9,10-dioxo-9,10-dihydroanthracen-1-yl)amino]propanamide
N;N-diethyl-3-[(4-{[2-(diethylcarbamoyl)ethyl]amino}-9,10-dioxo-9,10-dihydroanthracen-1-yl)amino]propanamide

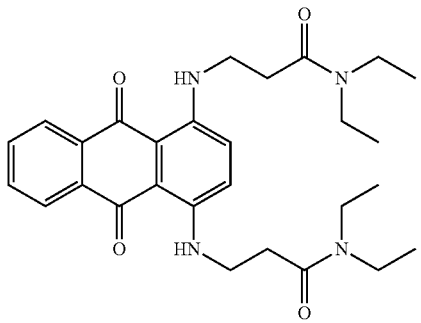 [SMILES: CCN(CC)C(=O)CCNc1ccc(NCCC(=O)N(CC)CC)c2c1C(=O)c1ccccc1C2=O]

The following compounds of formula (I) provide particularly intense blue-gray shades without a violet cast and are particularly suitable for matting keratin fibers. A further particularly preferred embodiment are therefore agents including at least one compound of formula (I) which is selected from
1,4-bis({[2-(2-hydroxyethoxy)ethyl]amino})-9,10-dihydroanthracene-9,10-dione
1,4-bis({[3-(2-hydroxyethoxy)propyl]amino})-9,10-dihydroanthracene-9,10-dione
1,4-bis({[2-(3-hydroxypropoxy)ethyl]amino})-9,10-dihydroanthracene-9,10-dione
1,4-bis({[3-(3-hydroxypropoxy)propyl]amino})-9,10-dihydroanthracene-9,10-dione
1,4-bis({2-[(2-hydroxyethyl)amino]ethyl}amino)-9,10-dihydroanthracene-9,10-dione
1,4-bis({2-[(3-hydroxypropyl)amino]ethyl}amino)-9,10-dihydroanthracene-9,10-dione
1,4-bis({3-[(2-hydroxyethyl)amino]propyl}amino)-9,10-dihydroanthracene-9,10-dione
1,4-bis({3-[(3-hydroxypropyl)amino]propyl}amino)-9,10-dihydroanthracene-9,10-dione
1,4-bis({2-[(2-aminoethyl)amino]ethyl}amino)-9,10-dihydroanthracene-9,10-dione
1,4-bis({3-[(2-aminoethyl)amino]propyl}amino)-9,10-dihydroanthracene-9,10-dione
1,4-bis({2-[(3-aminopropyl)amino]ethyl}amino)-9,10-dihydroanthracene-9,10-dione and
1,4-bis({3-[(3-aminopropyl)amino]propyl}amino)-9,10-dihydroanthracene-9,10-dione.
Within this group, the compounds
1,4-bis({[3-(2-hydroxyethoxy)propyl]amino})-9,10-dihydroanthracene-9,10-dione
1,4-bis({[3-(3-hydroxypropoxy)propyl]amino})-9,10-dihydroanthracene-9,10-dione
1,4-bis({3-[(2-hydroxyethyl)amino]propyl}amino)-9,10-dihydroanthracene-9,10-dione
1,4-bis({3-[(3-hydroxypropyl)amino]propyl}amino)-9,10-dihydroanthracene-9,10-dione
1,4-bis({3-[(2-aminoethyl)amino]propyl}amino)-9,10-dihydroanthracene-9,10-dione and
1,4-bis({3-[(3-aminopropyl)amino]propyl}amino)-9,10-dihydroanthracene-9,10-dione
are again explicitly particularly preferred since they have the strongest substantivity, the best matting performance and the best washing fastness.

The agents according to the invention for coloring and/or matting keratin fibers preferably include the compound(s) of formula (I) in quantities of above 1 ppm and below 10 wt. %, in each case relative to the entire agent. A preferred embodiment is here an agent which includes the compound(s) of formula (I) in a proportion of 0.001 to 5 wt. %, preferably of 0.0025 to 3.5 wt. %, more preferably of 0.005 to 2.5 wt. % and more preferably of 0.01 to 1.5 wt. %, in each case relative to the total weight of the agent.

In a further preferred embodiment, the agents according to the invention additionally include, in addition to the compound of formula (I), at least one further substantive dye. Substantive dyes may be subdivided into anionic, cationic and nonionic substantive dyes. The substantive dyes are preferably selected from nitrophenylenediamines, nitroaminophenols, azo dyes, anthraquinones, triarylmethane dyes or indophenols and the physiologically acceptable salts thereof. The additional substantive dyes are used in each case preferably in a proportion of 0.001 to 2 wt. %, relative to the entire preparation for use.

Preferred anionic substantive dyes are the compounds known by the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue. Preferred cationic substantive dyes are cationic triphenylmethane dyes, such as for example Basic Blue 7, Basic Blue 26, Basic Violet 2 and Basic Violet 14, aromatic systems which are substituted with a quaternary nitrogen group, such as for example Basic Yellow 57, Basic Red 76, Basic Blue 99, Basic Brown 16 and Basic Brown 17, cationic anthraquinone dyes, such as HC Blue 16 (Bluequat B) and substantive dyes which include a heterocycle which comprises at least one quaternary nitrogen atom, in particular Basic Yellow 87, Basic Orange 31 and Basic Red 51. The cationic substantive dyes distributed under the trademark Arianor are cationic substantive dyes which are likewise preferred according to the invention. Suitable nonionic substantive dyes are in particular nonionic nitro and quinone dyes and neutral azo dyes. Preferred nonionic substantive dyes are the compounds known by the international names or trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenol)amino]-benzoic acid, 4-[(3-hydroxypropyl)amino]-3-nitrophenol, 4-nitro-o-phenylenediamine 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-4-nitrophenol.

The compounds of formula (I) may be used in combination with all of the above-stated substantive dyes in agents for coloring and/or matting keratinic fibers, wherein coloring results with good fastness characteristics are obtained. Specific dye combinations, however, give rise to particularly long-lasting colorings such that these combinations are preferred.

It is more preferred for the compound(s) of formula (I) to be used in combination with Basic Yellow 57, Basic Red 76, Basic Brown 16 and Basic Brown 17, such as HC Blue 16 (Bluequat B), Basic Yellow 87, Basic Orange 31, Basic Red 51, HC Red 1, HC Red 3, HC Red 7, HC Red 10, HC Red 11, HC Red 13, HC Red BN, HC Blue 2, HC Blue 11, HC Blue 12, 2-amino-4-nitrophenol, 1,4-bis-(2-hydroxyethyl)amino-2-nitrobenzene, 3-nitro-4-(2-hydroxyethyl)aminophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 4-[(3-hydroxypropyl)amino]-3-nitrophenol and/or 4-nitro-o-phenylenediamine.

The agents according to the invention may furthermore also be used together with oxidation coloring agents. Such oxidation coloring agents additionally include at least one oxidation dye precursor, preferably at least one oxidation dye precursor of the developer type and at least one oxidation dye precursor of the coupler type. Particularly suitable oxidation dye precursors of the developer type are here selected from at least one compound from the group which is formed by p-phenylenediamine, p-tolylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4'-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one and the physiologically acceptable salts thereof.

Particularly suitable oxidation dye precursors of the coupler type are here selected from the group formed by 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy) ethanol, 1,3-bis-(2,4-diaminophenoxy)propane, 1-methoxy-2-amino-4-(2-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxy-ethyl)amino]-4,5-dimethylphenyl}amino)ethanol, 2-[3-morpholin-4-ylphenyl)-amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts thereof.

The additional substantive dyes, developer components and coupler components are preferably in each case used in a proportion of 0.0001 to 5.0 wt. %, preferably 0.001 to 3.5 wt. %, in each case relative to the ready-to-use agent. Developer components and coupler components are generally used in approximately molar quantities relative to one another. While molar use has also proven convenient, a certain excess of individual oxidation dye precursors is not disadvantageous, such that developer components and coupler components may be present in a molar ratio of 1:0.5 to 1:3, in particular 1:1 to 1:2.

A further preferred embodiment is an agent for coloring and/or matting keratinic fibers which is characterized in that it additionally includes, relative to the weight of the entire agent, in each case 0.001 to 5 wt. % of one or more oxidation dye precursors and/or substantive dyes.

If matting with the substantive dyes according to the invention and oxidative lightening of the keratin fibers is to proceed in one step, the agents according to the invention additionally include an oxidizing agent, preferably hydrogen peroxide and/or a solid addition product thereof onto organic or inorganic compounds.

In a preferred embodiment, hydrogen peroxide itself is used as an aqueous solution. The concentration of a hydrogen peroxide solution in the agent according to the invention is determined on the one hand by statutory requirements and on the other hand by the desired effect; 6 to 12 wt. % solutions in water are preferably used. Ready-to-use agents of the first subject matter of the invention which are preferred according to the invention are characterized in that, relative to the total weight of the ready-to-use agent, they include 0.5 to 20 wt. %, preferably 1 to 12.5 wt. %, more preferably 2.5 to 10 wt. % and in particular 3 to 6 wt. % of hydrogen peroxide, in each case relative to the total weight of the agent.

In order to achieve an enhanced brightening and bleaching action, the agent may furthermore include at least one peroxo salt. Suitable peroxo salts are inorganic peroxo compounds, preferably selected from the group formed by ammonium peroxodisulfate, alkali metal peroxodisulfates, ammonium peroxomonosulfate, alkali metal peroxomonosulfates, alkali metal peroxodiphosphates and alkaline earth metal peroxides. Peroxodisulfates, in particular ammonium peroxodisulfate, potassium peroxodisulfate and sodium peroxodisulfate, are more preferred.

The persulfates are in each case present in the agent according to the invention in a quantity of 0.5 to 20 wt. %, preferably 1 to 12.5 wt. %, more preferably 2.5 to 10 wt. % and in particular 3 to 6 wt. %, relative to the total weight of the ready-to-use agent.

The coloring and/or matting agent may include further bleach boosters in order to boost blonding action, such as for example tetraacetylethylenediamine (TAED), 1,5-diacetyl-2,4-dioxohexahydro-1,3,5-triazine (DADHT), tetraacetylglycoluril (TAGU), N-nonanoylsuccinimide (NOSI), n-nonanoyl- or isononanoyloxybenzenesulfonate (n- or i-NOBS), phthalic anhydride, triacetin, ethylene glycol diacetate and 2,5-diacetoxy-2,5-dihydrofuran and carbonate salts or hydrogencarbonate salts, in particular ammonium hydrogencarbonate, ammonium carbonate, sodium hydrogencarbonate, disodium carbonate, potassium hydrogencarbonate, dipotassium carbonate and calcium carbonate, and nitrogen-containing, heterocyclic bleach boosters, such as 4-acetyl-1-methylpyridinium p-toluenesulfonate, 2-acetyl-1-methylpyridinium p-toluenesulfonate, and N-methyl-3,4-dihydroisoquinolinium p-toluenesulfonate.

The ready-to-use coloring agents may furthermore include additional active substances, auxiliary substances and additives in order to improve coloring performance and adjust further desired properties of the agents.

The ready-to-use coloring agents are preferably provided as a liquid preparation and a surface-active substance is therefore additionally added to the agents, wherein such surface-active substances, depending on the area of application are described as surfactants or as emulsifiers: they are preferably selected from anionic, cationic, zwitterionic, amphoteric and nonionic surfactants and emulsifiers.

Agents which are preferred according to the invention are characterized in that the agent additionally includes at least one anionic surfactant. Preferred anionic surfactants are fatty acids, alkyl sulfates, alkyl ether sulfates and ether carboxylic acids with 10 to 20 C atoms in the alkyl group and up to 16 glycol ether groups per molecule. The anionic surfactants are used in proportions of 0.1 to 45 wt. %, preferably of 1 to 30 wt. % and particularly preferably of 1 to 15 wt. %, relative to the total quantity of the ready-to-use agent.

Agents which are preferred according to the invention are characterized in that the agent additionally includes at least one zwitterionic surfactant. Particularly suitable zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethylimidazolines. One preferred zwitterionic surfactant is known by the INCI name Cocamidopropyl Betaine.

Agents which are preferred according to the invention are characterized in that the agent additionally includes at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids. More preferred amphoteric surfactants are N-cocoalkyl aminopropionate, cocoacylaminoethyl aminopropionate and $C_{12}$-$C_{18}$ acylsarcosine.

It has furthermore proved advantageous for the agents to include further non-ionogenic interfacially active substances. Preferred nonionic surfactants have proved to be alkyl polyglycosides together with alkylene oxide addition products onto fatty alcohols and fatty acids with in each case 2 to 30 mol of ethylene oxide per mol of fatty alcohol or fatty acid respectively. Preparations having excellent properties are likewise obtained if they include fatty acid esters of ethoxylated glycerol as the nonionic surfactants.

The nonionic, zwitterionic or amphoteric surfactants are used in proportions of 0.1 to 45 wt. %, preferably of 1 to 30 wt. % and particularly preferably of 1 to 15 wt. %, relative to the total quantity of the ready-to-use agents.

Agents which are suitable according to the invention may also include cationic surfactants of the quaternary ammonium compound, ester quat and amidoamine type. Preferred quaternary ammonium compounds are ammonium halides and the imidazolium compounds known under the INCI names Quaternium-27 and Quaternium-83. Quaternized protein hydrolysates are further cationic surfactants which are usable according to the invention. One compound from the amidoamines which is particularly suitable according to the invention is stearamidopropyldimethylamine which is commercially available under the name Tegoamid® S 18. Preferred ester quats are quaternized ester salts of fatty acids with triethanolamine, quaternized ester salts of fatty acids with diethanolalkylamines and quaternized ester salts of fatty acids with 1,2-dihydroxypropyldialkylamines. The agents used according to the invention preferably include the cationic surfactants in proportions of 0.05 to 10 wt. %, relative to the total agent.

The ready-to-use coloring agents may include further auxiliary substances and additives. It has for instance proved advantageous for the agent to include at least one thickener. No restrictions apply in principle with regard to these thickeners. Both organic and purely inorganic thickeners may be used.

Suitable thickeners are anionic, synthetic polymers; cationic, synthetic polymers; naturally occurring thickeners, such as nonionic guar gums, scleroglucan gums or xanthan gums, gum arabic, gum ghatti, karaya gum, tragacanth gum, carrageenan gum, agar-agar, locust bean flour, pectins, alginates, starch fractions and derivatives such as amylose, amylopectin and dextrins, and cellulose derivatives, such as for example methylcellulose, carboxyalkylcelluloses and hydroxyalkylcelluloses; nonionic, completely synthetic polymers, such as polyvinyl alcohol or polyvinylpyrrolidinone; and inorganic thickeners, in particular phyllosilicates such as for example bentonite, particularly smectites, such as montmorillonite or hectorite.

Coloring processes on keratin fibers conventionally proceed in an alkaline environment. Establishing an excessively high pH value is, however, not desirable if the keratin fibers and also the skin are to be treated as gently as possible. It is therefore preferred for the pH value of the ready-to-use agent to be between 7 and 11, in particular between 8 and 10.5. The pH values for the purposes of the present invention are pH values which were measured at a temperature of 22° C.

Alkalizing agents usable for adjusting the preferred pH according to the invention may be selected from the group which is formed by ammonia, alkanolamines, basic amino acids, and inorganic alkalizing agents such as alkali(ne earth) metal hydroxides, alkali(ne earth) metal metasilicates, alkali (ne earth) metal phosphates and alkali(ne earth) metal hydrogenphosphates. Preferred inorganic alkalizing agents are magnesium carbonate, sodium hydroxide, potassium hydroxide, sodium silicate and sodium metasilicate. Organic alkalizing agents usable according to the invention are preferably selected from monoethanolamine, 2-amino-2-methylpropanol and triethanolamine. The basic amino acids usable as alkalizing agents according to the invention are preferably selected from the group formed by arginine, lysine, ornithine and histidine, more preferably arginine. It has, however, proved in the course of the investigations relating to the present invention that agents which are preferred according to the invention are furthermore characterized in that they additionally include an organic alkalizing agent. One embodiment of the first subject matter of the invention is characterized in that the agent additionally includes at least one alkalizing agent which is selected from the group which is formed from ammonia, alkanolamines and basic amino acids, in particular from ammonia, monoethanolamine and arginine or the acceptable salts thereof.

The agents according to the invention may moreover include further active substances, auxiliary substances and additives, such as for example nonionic polymers such as for example vinylpyrrolidinone/vinyl acrylate copolymers, polyvinylpyrrolidinone, vinylpyrrolidinone/vinyl acetate copolymers, polyethylene glycols and polysiloxanes; additional silicones such as volatile or non-volatile, straight-chain, branched or cyclic, crosslinked or uncrosslinked polyalkylsiloxanes (such as dimethicones or cyclomethicones), polyarylsiloxanes and/or polyalkylarylsiloxanes, in particular polysiloxanes with organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers; cationic polymers, such as quaternized cellulose ethers, polysiloxanes with quaternary groups, dimethyldiallylammonium chloride polymers, acrylamide-dimethyldiallylammonium chloride copolymers, dimethylaminoethylmethacrylate methosulfate-vinylpyrrolidinone copolymers quaternized with diethyl sulfate, vinylpyrrolidinone-imidazolinium methochloride copolymers and quaternized polyvinyl alcohol; zwitterionic and amphoteric polymers; anionic polymers such as for example polyacrylic acids or crosslinked polyacrylic acids; structuring agents such as glucose, maleic acid and lactic acid, hair-conditioning compounds, such as phospholipids, for example lecithin and cephalins; perfume oils, dimethyl isosorbide and cyclodextrins; active substances which improve fiber structure, in particular mono-, di- and oligosaccharides such as for example glucose, galactose, fructose, fruit sugar and lactose; dyes for coloring the agent; antidandruff active ingredients such as piroctone olamine, zinc omadine and climbazole; amino acids and oligopeptides; animal- or plant-based protein hydrolysates, as well as in the form of the fatty acid condensation products or optionally anionically or cationically modified derivatives thereof; vegetable oils; light stabilizers and UV blockers. A person skilled in the art will select these further substances in accordance with the desired properties of the agents. With regard to further optional components and the quantities of these components used, reference is explicitly made to the relevant handbooks known to a person skilled in the art. The additional active ingredients and auxiliaries are preferably used in the agents according to the invention in quantities of in each case 0.0001 to 25 wt. %, in particular of 0.0005 to 15 wt. %, relative to the total weight of the mixture for use.

The agents according to the invention are outstandingly suitable for producing intense blue shades, in particular for producing intense blue to gray shades, on keratinic fibers. In conjunction with their good fastness characteristics and good stability towards oxidizing agents such as hydrogen peroxide, they are therefore highly suitable for matting keratin fibers.

The present invention accordingly further provides the cosmetic use of an agent of the first subject matter of the invention for producing intense blue shades on keratin fibers and/or for matting keratin fibers during or after oxidative lightening.

The agents of the first subject matter of the invention may be used in methods for matting human hair. In a first embodiment of the method, the dyes of formula (I) according to the invention are applied after the blonding operation onto the keratin fibers in the form of a post-treatment agent, wherein the post-treatment agent may be a shampoo, a gel, a conditioner, a cream, a foaming solution, a mousse or an aerosol with the conventional previously described further ingredients. The period between the blonding or bleaching operation and use of the post-treatment agent may amount to some days to weeks. Preferably, however, the blonding operation and the matting proceed within the same day, in particular within a few hours. In one more preferred embodiment, post-treatment is carried out directly subsequent to the blonding operation.

The blonding agents are conventionally two-component products in which a component (A1) including oxidizing agent is mixed shortly before use with an (alkalizing) agent (A2) and this ready-to-use mixture is applied onto the hair.

The invention thus comprises a first method for matting human hair in which, directly before use, a cosmetic agent (A1) for oxidative lightening including 0.5 to 20 wt. % hydrogen peroxide is mixed with an agent (A2), this ready-to-use agent is applied onto the keratin fibers, left on the keratin fibers for a period of 5 to 60 minutes, preferably of 15 to 45 minutes, and then rinsed back out, the keratin fibers are optionally dried, and then a post-treatment agent (B) is applied onto the keratin fibers, left on the keratin fibers for a period of 2 to 45 minutes, preferably of 5 to 30 minutes, and then rinsed back out, wherein the agent (B) is an agent of the first subject matter of the invention.

In a further embodiment, the blonding or bleaching of the hair and matting operation may proceed in one step, such that the matting agent is applied together with the oxidative lightening agent onto the keratin fibers.

In this case, the blonding agent is preferably a two-component product in which a component (A1) including oxidizing agent is mixed shortly before use with an (alkalizing) agent (A2), wherein the agent (A2) additionally includes a compound of formula (I) according to the invention.

A second method according to the invention is thus one in which, directly before use, a cosmetic agent (A1) for oxidative lightening including 0.5 to 20 wt. % hydrogen peroxide is mixed with an agent (A2), this ready-to-use agent is applied onto the keratin fibers, left on the keratin fibers for a period of 5 to 60 minutes, preferably of 15 to 45 minutes, and then rinsed back out, and then a post-treatment agent (B) is applied onto the keratin fibers, left on the keratin fibers for a period of 2 to 45 minutes, preferably of 5 to 30 minutes, and then rinsed back out, wherein the agent (A2) is an agent of the first subject matter of the invention.

In order to boost the matting action, it is likewise conceivable for the dyes of formula (I) according to the invention to be used on the keratinic fibers not only during the blonding operation together with the oxidizing agent but also in the form of a post-treatment agent. The present invention accordingly further provides a method for matting keratinic fibers in which, directly before use, a cosmetic agent (A1) for oxidative lightening including 0.5 to 20 wt. % hydrogen peroxide is mixed with an agent (A2), this ready-to-use agent is applied onto the keratin fibers, left on the keratin fibers for a period of 5 to 60 minutes, preferably of 15 to 45 minutes, and then rinsed back out, and then a post-treatment agent (B) is applied onto the keratin fibers, left on the keratin fibers for a period of 2 to 45 minutes, preferably of 5 to 30 minutes, and then rinsed back out, wherein the agent (A2) and/or the agent (B) is an agent of the first subject matter of the invention.

During the period of exposure of the fiber to the agent it may be advantageous to assist the lightening process or matting process by supplying heat. Heat may be supplied by an external heat source, such as for example hot air from a hot air blower, and also, in particular when lightening the hair of a living test subject, by the body temperature of the test subject. In the case of the latter possibility, the treated part is conventionally covered with a cap. Exposure at room temperature is likewise according to the invention. In particular, the temperature during the period of exposure is between 20° C. and 40° C., in particular between 25° C. and 38° C. After the end of the period of exposure, the remaining coloring preparation is rinsed out of the hair with water or a cleaning agent. Conventional commercial shampoo may in particular be used here as the cleaning agent, wherein it is in particular possible to dispense with the cleaning agent and carry out the rinsing operation with water if the lightening agent has a carrier with a high surfactant content. The agents according to the invention may be formulated and correspondingly used as a single component agent (matting and lightening agent) or as a multicomponent agent such as a two-component agent or three-component agent. Separation into multicomponent systems may in particular be considered where incompatibilities of the ingredients are to be expected or feared; in such systems, the agent for use is produced by the consumer directly before application by mixing the components.

The above statements regarding the agents according to the invention apply mutatis mutandis with regard to further preferred embodiments of the use and methods according to the invention.

EXAMPLES

1. Synthesis Examples 1.1. Synthesis Example 1

Synthesis of 1,4-bis({2-[(2-hydroxyethyl)amino]ethyl}-amino)-9,10-dihydroanthracene-9,10-dione (substantive dye 1)

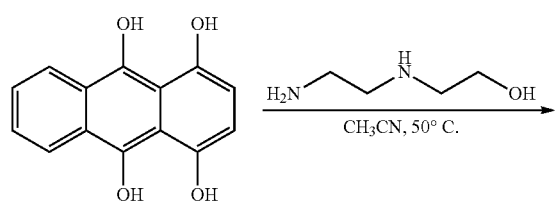

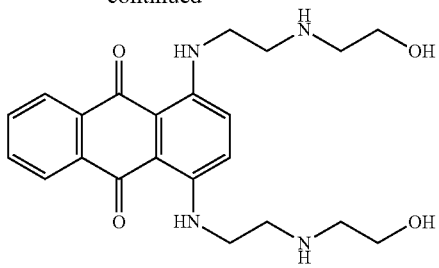

62.7 g (0.45 mol) of 2-(2-aminoethylamino)ethanol were added to a solution of 10.0 g (40.0 mmol) of leucoquinizarin (9,10-dihydroxy-2,3-dihydroanthracene-1,4-dione) in 100 ml of acetonitrile and the reaction mixture was stirred for 1 h at 50° C. under a nitrogen atmosphere. Air was then blown through the solution for 1 h at 50° C. with stirring. The reaction mixture was then combined with 100 ml of acetonitrile, cooled to 15° C. and the precipitated solid filtered out. The latter was rewashed with copious ethanol and then dried under a vacuum. 1,4-Bis({3-[(2-hydroxyethyl)amino]ethyl}amino)-9,10-dihydroanthracene-9,10-dione (substantive dye 1) was obtained as a black powder (15.5 g, 37.0 mmol, 94%).

$^1$H NMR (300 MHz, d$_6$-DMSO): δ=2.65 (m, 4H, CH$_2$), 2.83 (m, 4H, CH$_2$), 3.49 (m, 8H, CH$_2$), 4.51 (br s, 2H, NH), 7.50 (s, 2H, Ar—H), 7.74 (m, 2H, Ar—H), 8.23 (m, 2H, Ar—H), 10.92 (m, 2H, NH)

1.2 Synthesis Example 2

1,4-bis({2-[(3-hydroxypropyl)amino]ethyl}amino)-9,10-dihydroanthracene-9,10-dione (substantive dye 2)

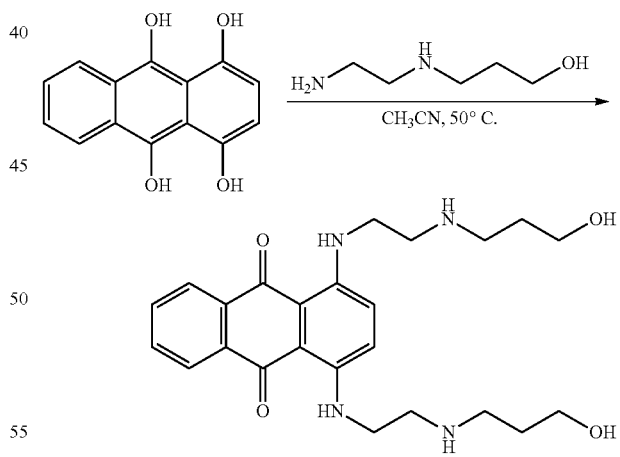

48.0 g (0.41 mol) of 3-(2-aminoethylamino)ethanol were added to a solution of 10.0 g (40.0 mmol) of leucoquinizarin (9,10-dihydroxy-2,3-dihydroanthracene-1,4-dione) in 100 ml of acetonitrile and the reaction mixture was stirred for 1 h at 50° C. under a nitrogen atmosphere. Air was then blown through the solution for 1 h at 50° C. with stirring. The reaction mixture was then combined with 100 ml of acetonitrile, cooled to 15° C. and the precipitated solid filtered out. The latter was rewashed with copious ethanol and then dried under a vacuum. 1,4-Bis({3-[(2-hydroxypropyl)amino]

ethyl}amino)-9,10-dihydroanthracene-9,10-dione (substantive dye 2) was obtained as a dark blue powder (3.3 g, 7.5 mmol, 19%).

$^1$H NMR (300 MHz, d$_6$-DMSO): δ=1.54 (m, 4H, CH$_2$), 2.67 (m, 4H, CH$_2$), 2.85 (m, 4H, CH$_2$), 3.50 (m, 8H, CH$_2$), 4.61 (br s, 4H, NH, OH), 7.47 (s, 2H, Ar—H), 7.72 (m, 2H, Ar—H), 8.21 (m, 2H, Ar—H), 10.92 (m, 2H, NH)

1.3. Synthesis Example 3

Synthesis of 9,4-bis({3-[(4-hydroxyethyl)amino]-propyl}amino)-3,10-dihydroanthracene-9,10-dione (substantive dye 3)

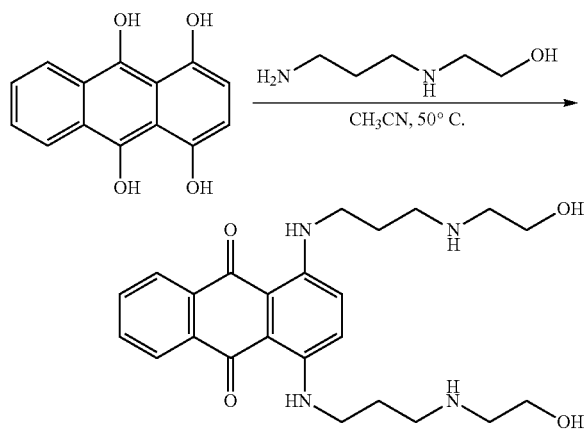

27.0 g (0.23 mol) of 2-(3-aminoethylamino)ethanol were added to a solution of 10.0 g (40.0 mmol) of leucoquinizarin (9,10-dihydroxy-2,3-dihydroanthracene-1,4-dione) in 100 ml of acetonitrile and the reaction mixture was stirred for 1 h at 50° C. under a nitrogen atmosphere. Air was then blown through the solution for 1 h at 50° C. with stirring. The reaction mixture was then combined with 100 ml of acetonitrile, cooled to 15° C. and the precipitated solid filtered out. The latter was rewashed with copious ethanol and then dried under a vacuum. 1,4-Bis({3-[(2-hydroxyethyl)amino]propyl}amino)-9,10-dihydroanthracene-9,10-dione (substantive dye 3) was obtained as a dark blue powder (18.1 g, 7.5 mmol, 99%).

$^1$H NMR (300 MHz, d$_6$-DMSO): δ=1.74 (m, 4H, CH$_2$), 2.57 (m, 4H, CH$_2$), 2.63 (m, 4H, CH$_2$), 3.49 (m, 8H, CH$_2$), 7.42 (s, 2H, Ar—H), 7.74 (m, 2H, Ar—H), 8.22 (m, 2H, Ar—H), 10.87 (m, 2H, NH)

1.4. Synthesis Example 4

Synthesis of 1,4-bis({3-[(3-hydroxypropyl)amino]-propyl}amino)-9,10-dihydroanthracene-9,10-dione (substantive dye 4)

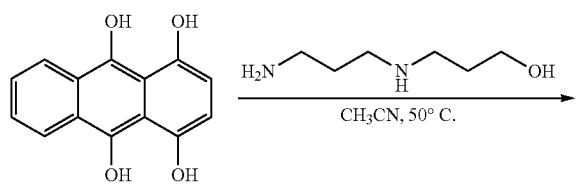

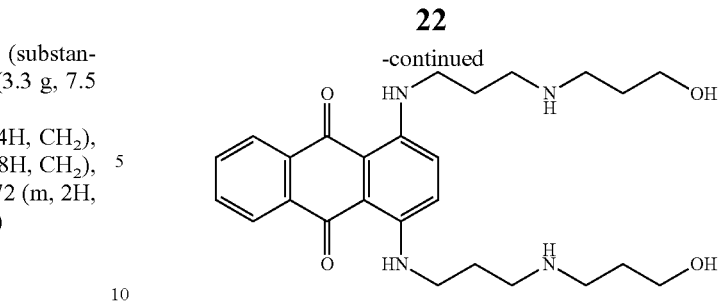

60.0 g (0.45 mol) of 3-(3-aminoethylamino)propanol were added to a solution of 10.0 g (40.0 mmol) of leucoquinizarin (9,10-dihydroxy-2,3-dihydroanthracene-1,4-dione) in 100 ml of acetonitrile and the reaction mixture was stirred for 1 h at 50° C. under a nitrogen atmosphere. Air was then blown through the solution for 1 h at 50° C. with stirring. The reaction mixture was then combined with 100 ml of acetonitrile, cooled to 15° C. and the precipitated solid filtered out. The latter was rewashed with copious ethanol and then dried under a vacuum. 1,4-Bis({3-[(3-hydroxypropyl)amino]propyl}amino)-9,10-dihydroanthracene-9,10-dione (substantive dye 4) was obtained as a dark blue powder (17.1 g, 7.5 mmol, 91%).

$^1$H NMR (300 MHz, d$_6$-DMSO): δ=1.750 (m, 4H, CH$_2$), 1.72 (m, 4H, CH$_2$), 2.50 (m, 4H, CH$_2$), 2.68 (m, 4H, CH$_2$), 3.41 (m, 8H, CH$_2$), 7.41 (s, 2H, Ar—H), 7.78 (m, 2H, Ar—H), 8.24 (m, 2H, Ar—H), 10.82 (m, 2H, NH)

1.5. Synthesis Example 5

Synthesis of 1,4-bis({2-[(2-aminoethyl)amino]ethyl}-amino)-9,10-dihydroanthracene-9,10-dione (substantive dye 5)

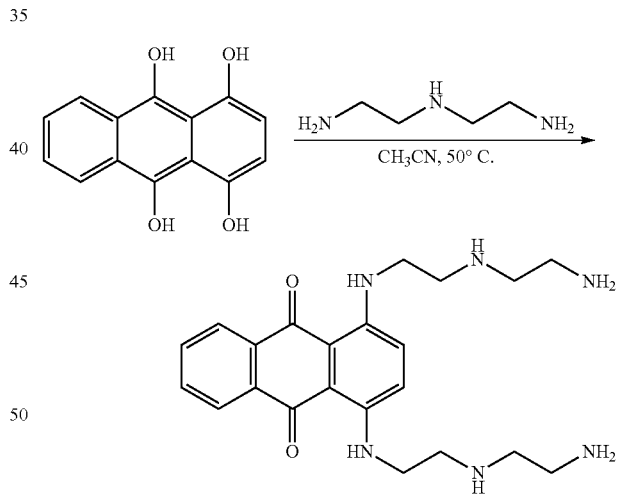

46.1 g (0.45 mol) of diethylenetriamine were added to a solution of 10.0 g (40.0 mmol) of leucoquinizarin (9,10-dihydroxy-2,3-dihydroanthracene-1,4-dione) in 100 ml of acetonitrile and the reaction mixture was stirred for 1 h at 50° C. under a nitrogen atmosphere. Air was then blown through the solution for 1 h at 50° C. with stirring. The reaction mixture was then combined with 100 ml of acetonitrile, cooled to 15° C. and the precipitated solid filtered out. The latter was rewashed with copious ethanol and then dried under a vacuum. 1,4-Bis({3-[(2-aminoethyl)amino]ethyl}amino)-9,10-dihydroanthracene-9,10-dione (substantive dye 5) was obtained as a deep blue powder (4.4 g, 10.7 mmol, 27%).

$^1$H NMR (300 MHz, d$_6$-DMSO): δ=2.47 (m, 8H, CH$_2$), 2.53 (m, 8H, CH$_2$), 7.39 (s, 2H, Ar—H), 7.72 (m, 2H, Ar—H), 8.19 (m, 2H, Ar—H), 10.88 (m, 2H, NH)

2. Coloring Examples

2.1 Production of the Coloring Creams

The following coloring creams were produced:

2.1.1 Coloring Cream 1 (Nonionic Coloring Cream)

| | |
|---|---|
| Cetearyl alcohol | 6.0 g |
| Coconut Alcohol | 6.0 g |
| PEG-40 Hydrogenated Castor Oil | 1.0 g |
| Ceteareth-12 | 3.0 g |
| Ceteareth-20 | 3.0 g |
| PHB methyl ester | 0.3 g |
| PHB propyl ester | 0.2 g |
| Phenoxyethanol | 1.0 g |
| PEG-8 | 5.0 g |
| Substantive dye according to the invention | 1.0 g |
| Ammonium sulfate | 1.0 g (in 30.0 g of water) |
| Hydroxyethylcellulose | 1.0 g (in 15.0 g of water) |
| NaOH 0.1% | Ad pH value |
| Water | Ad 100 |

The first nine components were melted together at 80° C. This mixture was emulsified with an aqueous solution of the substantive dye and of the ammonium sulfate in 30 g of water. A swelled preparation of 1.0 g of Natrosol 250 HR in 15.0 g of water was then added. The stated pH value was adjusted with 0.1% sodium hydroxide solution and then the mixture was made up to 100 g with water.

2.1.2 Coloring Cream 2 (Cationic Coloring Cream)

| | |
|---|---|
| Cetearyl alcohol | 4.0 g |
| Ceteareth-12 | 1.0 g |
| Dehyquart ® A-CA | 2.0 g |
| Ammonium sulfate | 1.0 g (in 30.0 g of water) |
| Substantive dye according to the invention | 1.0 g |
| Water | Ad 100 |

The first three components were melted together, after which the melt was emulsified with hot water. The dye predissolved or predispersed in water and the aqueous ammonium sulfate solution were then added. The pH value was adjusted to the stated value with ammonia or citric acid and then the mixture was made up to 100 g with water.

2.1.3 Coloring Cream 3 (Anionic Coloring Cream)

| | |
|---|---|
| Cetearyl alcohol | 1.0 g |
| Coconut Alcohol | 1.0 g |
| Akypo Soft ® RLM 45N | 1.1 g |
| PHB propyl ester | 0.1 g |
| PHB methyl ester | 0.1 g |
| Ammonium sulfate | 1.0 g (in 30.0 g of water) |
| Substantive dye according to the invention | 1.0 g |
| Water | Ad 100 |

The first five components were melted together. This melt was emulsified with hot water, then the dye predissolved or predispersed in water was added thereto and the ammonium sulfate solution added. The stated pH value was adjusted with ammonia or citric acid and then the mixture was made up to 100 g with water.

2.2 List of Raw Materials Used

Akypo RLM 45 NV® Lauryl alcohol 4.5-EO acetic acid sodium salt (min. active substance content 22%; INCI name: Sodium Laureth-5 Carboxylate)

Dehyquart® A-CA Trimethylhexadecylammonium chloride (approx. 24-26% active substance; INCI name: Aqua (Water), Cetrimonium Chloride)

2.3 Coloring 1.8 g portions of the coloring cream were applied onto approx. 6 cm long strands of human hair (Kerling natural European hair, blond) and left there for 30 minutes at 30° C. On completion of the period of exposure, the hair was rinsed, washed with a conventional shampoo and then dried. The strands of hair were colored in the shades stated below.

Substantive dye 1: 1,4-bis({2-[(2-hydroxyethyl)amino]ethyl}amino)-9,10-dihydroanthracene-9,10-dione
Substantive dye 2: 1,4-bis({2-[(3-hydroxypropyl)amino]ethyl}amino)-9,10-dihydroanthracene-9,10-dione
Substantive dye 3: 1,4-bis({3-[(2-hydroxyethyl)amino]propyl}amino)-9,10-dihydroanthracene-9,10-dione
Substantive dye 4: 1,4-bis({3-[(3-hydroxypropyl)amino]propyl}amino)-9,10-dihydroanthracene-9,10-dione
Substantive dye 5: 1,4-bis({2-[(2-aminoethyl)amino]ethyl}amino)-9,10-dihydroanthracene-9,10-dione

TABLE 1

| Dye | Coloring cream | pH | Color shade | Color intensity |
|---|---|---|---|---|
| Substantive dye 1 | 1 | 9.5 | storm blue (gray-blue) | ++ |
| Substantive dye 1 | 2 | 9.5 | storm blue (gray-blue) | ++ |
| Substantive dye 1 | 3 | 9.5 | storm blue (gray-blue) | + |
| Substantive dye 2 | 1 | 9.5 | grayish matt blue | ++ |
| Substantive dye 2 | 2 | 9.5 | gray-blue | ++ |
| Substantive dye 2 | 3 | 9.5 | Copenhagen blue | ++ |
| Substantive dye 3 | 1 | 9.5 | enamel blue | +++ |
| Substantive dye 3 | 2 | 9.5 | gray-blue | ++ |
| Substantive dye 3 | 3 | 9.5 | gray-blue | +++ |
| Substantive dye 4 | 1 | 9.5 | gray-blue | ++ |
| Substantive dye 4 | 2 | 9.5 | deep blue | +++ |
| Substantive dye 4 | 3 | 9.5 | ultramarine blue | +++ |
| Substantive dye 5 | 1 | 9.5 | matt blue-storm blue | + |
| Substantive dye 5 | 2 | 9.5 | storm blue (gray-blue) | ++ |
| Substantive dye 5 | 3 | 9.5 | dark blue | ++ |

Color intensity:
+ = clearly visible
++ = good
+++ = very good

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:
1. An agent for coloring and/or matting keratinic fibers, including in a cosmetic carrier at least one 1,4-diaminoanthraquinone derivative selected from the group consisting of
1,4-bis[(2-methoxyethyl)amino]-9,10-dihydroanthracene-9,10-dione
1,4-bis[(2-ethoxyethyl)amino]-9,10-dihydroanthracene-9,10-dione

1,4-bis[2-propoxyethyl)amino]-9,10-dihydroanthracene-9,10-dione
1,4-bis[(3-methoxypropyl)amino]-9,10-dihydroanthracene-9,10-dione
1,4-bis[(3-ethoxypropyl)amino]-9,10-dihydroanthracene-9,10-dione
1,4-bis[(3-propoxypropyl)amino]-9,10-dihydroanthracene-9,10-dione
6-methoxy-1,4-bis[(2-methoxyethyl)amino]-9,10-dihydroanthracene-9,10-dione
6-methoxy-1,4-bis[(2-ethoxyethyl)amino]-9,10-dihydroanthracene-9,10-dione
6-methoxy-1,4-bis[(2-propoxyethyl)amino]-9,10-dihydroanthracene-9,10-dione
6-methoxy-1,4-bis[(3-methoxypropyl)amino]-9,10-dihydroanthracene-9,10-dione
6-methoxy-1,4-bis[(3-ethoxypropyl)amino]-9,10-dihydroanthracene-9,10-dione
6-methoxy-1,4-bis[(3-propoxypropyl)amino]-9,10-dihydroanthracene-9,10-dione
1,4-bis({[2-(2-hydroxyethoxyl)ethyl]amino})-9,10-dihydro anthracene-9,10-dione
1,4-bis({[3-(2-hydroxyethoxy)propyl]amino})-9,10-dihydroanthracene-9,10-dione
1,4-bis({[2-(3-hydroxypropoxy)ethyl]amino})-9,10-dihydroanthracene-9,10-dione
1,4-bis({[3-(3-hydroxypropoxyl)propyl]amino})-9,10-dihydroanthracene-9,10-dione
6-methoxy-1,4-bis({[2-(2-hydroxyethoxy)ethyl]amino})-9,10-dihydroanthracene-9,10-dione
6-methoxy-1,4-bis({[3-(2-hydroxyethoxy)propyl]amino})-9,10-dihydroanthracene-9,10-dione
6-methoxy-1,4-bis({[3-(3-hydroxypropoxy)ethyl]amino})-9,10-dihydroanthracene-9,10-dione
6-methoxy-1,4-bis({[3-(3-hydroxypropoxy)propyl]amino})-9,10-dihydroanthracene-9,10-dione
1,4-bis({2-[(2-hydroxyethyl)amino]ethyl}amino)-9,10-dihydroanthracene-9,10-dione
1,4-bis({2-[(3-hydroxypropyl)amino]ethyl}amino)-9,10-dihydroanthracene-9,10-dione
1,4-bis({3-[(2-hydroxyethyl)amino]propyl}amino)-9,10-dihydroanthracene-9,10-dione
1,4-bis({3-[(3-hydroxypropyl)amino]propyl}amino)-9,10-dihydroanthracene-9,10-dione
1,4-bis({2-[(2-aminoethyl)amino]ethyl}amino)-9,10-dihydroanthracene-9,10-dione
1,4-bis({2-[(3-aminopropyl)amino]ethyl}amino)-9,10-dihydroanthracene-9,10-dione
1,4-bis({3-[(2-aminoethyl)amino]propyl}amino)-9,10-dihydroanthracene-9,10-dione
1,4-bis({3-[(3-aminopropyl)amino]propyl}amino)-9,10-dihydroanthracene-9,10-dione
N-methyl-3-[(4-{[2-(methylcarbamoyl)ethyl]amino}-9,10-dioxo-9,10-dihydroanthracen-1-yl)amino]propanamide
N-methyl-4-[(4-{[3-(methylcarbamoyl)propyl]amino}-9,10-dioxo-9,10-dihydroanthracen-1-yl)amino]butanamide
N-ethyl-3-[(4-{[2-(ethylcarbamoyl)ethyl]amino}-9,10-dioxo-9,10-dihydroanthracen-1-yl)amino]propanamide
N;N-dimethyl-3-[(4-{[2-(dimethylcarbamoyl)ethyl]amino}-9,10-dioxo-9,10-dihydroanthracen-1-yl)amino]propanamide and
N;N-diethyl-3-[(4-{[2-(diethylcarbamoyl)ethyl]amino}-9,10-dioxo-9,10-dihydroanthracen-1-yl)amino]propanamide.

2. The agent according to claim 1, characterized in that it includes the at least one 1,4-diaminoanthraquinone derivative in a proportion of 0.001 to 5 wt. % relative to the total weight of the agent.

3. The agent according to claim 1, characterized in that it additionally includes in each case 0.001 to 5 wt. % of one or more oxidation dye precursors and/or substantive dyes.

4. The agent according to claim 1, characterized in that the at least one 1,4-diaminoanthraquinone derivative is selected from the group consisting of
1,4-bis({[3-(2-hydroxyethoxy)propyl]amino})-9,10-dihydroanthracene-9,10-dione
1,4-bis({[3-(3-hydroxypropoxy)propyl]amino})-9,10-dihydroanthracene-9,10-dione
1,4-bis({3-[(2-hydroxyethyl)amino]propyl}amino)-9,10-dihydroanthracene-9,10-dione
1,4-bis({3-[(3-hydroxypropyl)amino]propyl}amino)-9,10-dihydroanthracene-9,10-dione
1,4-bis({3-[(2-aminoethyl)amino]propyl}amino)-9,10-dihydroanthracene-9,10-dione and
1,4-bis({3-[(3-aminopropyl)amino]propyl}amino)-9,10-dihydroanthracene-9,10-dione
and further includes at least one further substantive dye selected from the group consisting of Basic Blue 7, Basic Blue 26, Basic Violet 2, Basic Violet 14, Basic Blue 99 and HC Blue 16 (Bluequat B).

5. The agent according to claim 1, characterized in that the at least one 1,4-diaminoanthraquinone derivative is selected from the group consisting of
1,4-bis({[3-(2-hydroxyethoxy)propyl]amino})-9,10-dihydroanthracene-9,10-dione
1,4-bis({[3-(3-hydroxypropoxy)propyl]amino})-9,10-dihydroanthracene-9,10-dione
1,4-bis({3-[(2-hydroxyethyl)amino]propyl}amino)-9,10-dihydroanthracene-9,10-dione
1,4-bis({3-[(3-hydroxypropyl)amino]propyl}amino)-9,10-dihydroanthracene-9,10-dione
1,4-bis({3-[(2-aminoethyl)amino]propyl}amino)-9,10-dihydroanthracene-9,10-dione and
1,4-bis({3-[(3-aminopropyl)amino]propyl}amino)-9,10-dihydro anthracene-9,10-dione
and further includes at least one further substantive dye selected from the group consisting of HC Blue 2, HC Blue 11, HC Blue 12, Disperse Blue 3, HC Violet 1, Disperse Violet 1, Disperse Violet 4 and Disperse Black 9.

6. The agent according to claim 1, characterized in that it has a pH value of between 7 and 11.

7. The agent according to claim 1, characterized in that it includes at least one alkalizing agent selected from the group consisting ammonia, monoethanolamine, 2-amino-2-methylpropanol and triethanolamine.

8. The agent according to claims 1, characterized in that it additionally includes one or more cationic surfactants in a total quantity of 0.05 to 10 wt. %, relative to the total weight of the agent.

9. A method for matting keratinic fibers in which, directly before use,
a cosmetic agent (A1) for oxidative lightening including 0.5 to 20 wt. % hydrogen peroxide is mixed with
an agent (A2),
this ready-to-use agent is applied onto the keratin fibers, left on the keratin fibers for a period of 5 to 60 minutes, and then rinsed back out, and
then a post-treatment agent (B) is applied onto the keratin fibers, left on the keratin fibers for a period of 2 to 45 minutes, and then rinsed back out, wherein the agent (A2) and/or the agent (B) includes in a cosmetic carrier at least one 1,4-diaminoanthraquinone derivative of formula (I),

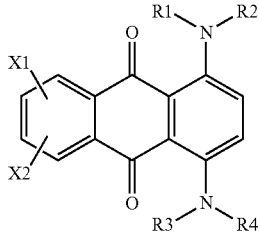

in which

R1, R3 mutually independently denote a hydrogen atom, a $C_1$-$C_6$ alkyl group, a $C_2$-$C_6$ alkenyl group, a hydroxy-$C_2$-$C_6$-alkyl group, a polyhydroxy-$C_2$-$C_6$-alkyl group, a cyano-$C_1$-$C_6$-alkyl group, a halo-$C_1$-$C_6$-alkyl group, an aryl-$C_1$-$C_6$-alkyl group, a heteroaryl-($C_1$-$C_6$)-alkyl group, an aryl group, a heteroaryl group, an amino-($C_2$-$C_6$)-alkyl group, a $C_1$-$C_6$-alkylamino-$C_2$-$C_6$-alkyl group or a $C_1$-$C_6$-dialkylamino-$C_2$-$C_6$-alkyl group, R2, R4 mutually independently denote a grouping of formula (II), $$—(CH_2)_n—Y1\text{-}(CH_2)_m—Y2 \qquad (II)$$

in which

Y1 denotes an oxygen atom (—O—), a sulfur atom (—S—), an amide group —CONR5- or a group —NR5-, Y2 denotes a hydrogen atom, a $C_2$-$C_6$ alkenyl group, a hydroxyl group, a $C_1$-$C_6$ alkoxy group, a hydroxy-$C_2$-$C_6$-alkoxy group or a group —NR5R6, n denotes an integer from 2 to 6, m denotes an integer from 1 to 6, R5, R6 mutually independently denote a hydrogen atom, a $C_1$-$C_6$ alkyl group, a $C_2$-$C_6$ alkenyl group, or a hydroxy-$C_2$-$C_6$-alkyl group, and X1, X2 mutually independently denote a hydrogen atom, a hydroxyl group, a $C_1$-$C_6$ alkoxy group, a $C_1$-$C_6$ alkyl group, a $C_2$-$C_6$ alkenyl group, a hydroxy-$C_2$-$C_6$-alkyl group, a polyhydroxy-$C_2$-$C_6$-alkyl group, a cyano-$C_1$-$C_6$-alkyl group, an amino group, a $C_1$-$C_6$-alkylamino group, a di-$C_1$-$C_6$-alkylamino group, an amino-($C_2$-$C_6$)-alkyl group, a $C_1$-$C_6$-alkylamino-$C_2$-$C_6$-alkyl group, a di-$C_1$-$C_6$-alkylamino-$C_2$-$C_6$-alkyl group, a $C_1$-$C_6$-alkoxy-$C_2$-$C_6$-alkyl group, a $C_1$-$C_6$-alkoxy-$C_2$-$C_6$-alkyloxy group, a nitro group, a carboxy group, a sulfonic acid group or a halogen atom.

\* \* \* \* \*